United States Patent [19]
Keller et al.

[11] Patent Number: 5,389,541
[45] Date of Patent: Feb. 14, 1995

[54] ERYTHROPOIETIN-DEPENDENT ERYTHROBLASTOID MOUSE CELL LINE

[75] Inventors: Gordon Keller, Denver, Colo.; Harmut Beug; Erwin Wagner, both of Vienna, Austria

[73] Assignee: Boehringer Ingelheim International GmbH, Ingelheim am Rhein, Germany

[21] Appl. No.: 952,880

[22] PCT Filed: May 28, 1991

[86] PCT No.: PCT/EP91/00981
§ 371 Date: Feb. 18, 1993
§ 102(e) Date: Feb. 18, 1993

[87] PCT Pub. No.: WO91/18973
PCT Pub. Date: Dec. 12, 1991

[30] Foreign Application Priority Data
Jun. 1, 1990 [DE] Germany .................. 4017679

[51] Int. Cl.⁶ .................. C12N 5/06; C12N 15/00
[52] U.S. Cl. .................. 435/240.2; 435/7.2; 435/7.21; 435/7.4
[58] Field of Search .................. 435/6, 240.2, 172.3, 435/4, 240.21, 7.2, 7.21, 7.4

[56] References Cited
PUBLICATIONS

Keller et al. 1989. Genes and Development 3:827-837.
Lewis et al. 1989. Exp. Hematol. 17:102-105.
Amersham Corp., Life Sciences Products Cataloge, 1989/90 Ed. p. 40.

*Primary Examiner*—Elizabeth C. Weimar
*Assistant Examiner*—Brian R. Stanton
*Attorney, Agent, or Firm*—D. E. Frankhouser; A. R. Stempel; M-E. M. Timbers

[57] ABSTRACT

The invention includes a mouse erythroblastoid cell line whose growth is responsive to levels of erythropoietin present in the cell line's growth medium. Also disclosed are methods of using the mouse erythroblastoid cell line to assay the amount of erythropoietin that is present in a sample.

1 Claim, 7 Drawing Sheets

ERYTHROPOIETIN-DEPENDENT ERYTHROBLASTOID MOUSE CELL LINE

The present invention relates to new erythroblastoid mouse cell lines.

The properties of lethally irradiated mice, reconstituted over a long period of time with bone marrow cells which express the src gene (after infection with the N-TK-v-src retrovirus) are already known (Keller and Wagner, 1989). Primary recipient mice of this kind develop a severe myeloproliferative disease characterised by a large number of erythroid precursor cells (in addition to increased numbers of precursor cells of other lineages).

Attempts to cultivate such cells in vitro have not hitherto resulted in the establishment of permanent haematopoietic cell lines.

The aim of the present invention was to provide erythroblastoid cell lines having specific properties.

This aim was achieved by transferring spleen cells from primary recipient animals once again into lethally irradiated mice (secondary recipient animals). To do this, nucleus-containing spleen cell preparations (i.e. those free from erythrocytes) were injected intravenously into lethally irradiated CBA mice (Keller and Wagner, 1989). Three week later the secondary recipient animals were killed and cells from spleen and bone marrow were cultivated in the presence of interleukin-3 (IL-3) and human recombinant erythropoietin (EPO). After 10 days, in addition to normally differentiated colonies of erythroid and myeloid origin, large colonies consisting of undifferentiated, blast-like cells developed in these cultures. These colonies could not be found in corresponding bone marrow cultures of control animals. A fairly large number of these colonies were isolated and expanded in the presence of EPO and IL-3. After an initial period of slow growth, some of the cultures obtained were able to be grown into mass cultures and finally established as cell lines. In view of the fact that they originate from individual colonies they can be regarded as clonal.

It was found, surprisingly, that the cell lines thus obtained survive and proliferate exclusively in the presence of erythropoietin. This strict dependency on EPO was found in all the cell lines investigated, the degree of EPO dependency being found to differ. EPO dependency can therefore be regarded as a characteristic feature of these cell lines which express the src oncogene.

The present invention thus relates to new erythroblastoid mouse cell lines which express the src gene and which are strictly erythropoietin-dependent for their survival and proliferation.

According to investigations which included three further cell lines in addition to the cell line designated E 4 and E 31 which were first to be characterised, it was found that the cell line E 31 shows the greatest EPO dependency. The other cell lines are dependent on erythropoietin to varying degrees. All in all, it was established by means of the experiments carried out that the dependency on erythropoietin is a common feature of cell lines which express the src oncogene.

The result that the cell lines E 4 and E 31 respond strongly to erythropoietin, a growth factor which acts specifically on late erythroid precursor cells, led one to assume that the cells of the erythroid lineage can be put down to haematopoietic differentiation or at least represent determined erythroid precursor cells (committed progenitors). In order to demonstrate this, the cells were investigated for two markers specific to erythroid cells, namely haemoglobin and the mamalian-homologous histone protein (presumably H1-0) of the erythroid-specific hen's histone H5.

The investigations into haemoglobin production and the presence of the mammalian homolog of histone H5 clearly showed that the cells of lines E 4 and E 31 belong to the erythroid lineage.

In order to demonstrate that all cells of cell lines E 4 and E 31 are of erythroid descent, attempts were made to induce haemoglobin production by means of chemicals. Whereas other erythroleukaemic mouse cell lines such as Friend cells (Orkin et al., 1975) can be induced by means of 2% DMSO to produce haemoglobin in more than 80% of cells, hen's erythroblast cell lines transformed with tyrosine kinase oncogenes (such as v-erbB; Beug et al., 1982a) can be induced by means of butyric acid (0.4 mM; Beug et al., 1982b) to express haemoglobin in more than 90% of the cells. These results show that the erythroblast cell lines which express v-src according to the invention are clearly different from mouse erythroleukaemia cell lines which are induced by the Friend leukaemia virus (FLV) or the Rauscher mouse leukaemia virus (R-Mulv) and show more similarity to hen's erythroblasts which are transformed with tyrosine kinase oncogenes, although these hen's erythroblasts, unlike the src-mammalian erythroblasts according to the invention, are always independent of erythropoietin for their survival and replication (Beug et al., 1982a, 1985).

In addition, the cells were tested by incubating them with various monoclonal antibodies. The antibodies used were those which recognise myeloid-specific cell surface antigens, antigens of pluripotent stem cells or (as a control) an antigen which is present on all haematopoietic cells apart from erythrocytes. The results obtained with the monoclonal antibodies rule out the possibility of the cell lines E 4 and E 31 containing cells other than those of the erythroid lineage.

Erythropoietin (EPO) is a growth factor which acts specifically on late erythroid precursor cells. Human erythropoietin was first produced in pure form in 1977 (Miyake et al., 1977). Erythropoietin is an acidic, relatively heat resistant and pH-stable glycoprotein. The primary and secondary structure coincides with that of mouse erythropoietin to a degree of 80 to 85%. Human EPO has a relative molecular mass of about 30,000; the protein content is 60% and consists of a single protein chain of 165 amino acids. From the primary translation product, 28 amino acids are cleaved before the hormone is released from the cell. The erythropoietin molecules in the blood show slight differences in their glycosylation.

The partial clarification of the amino acid sequence made it possible to isolate genomic and cDNA and, subsequently, to produce recombinant erythropoietin in eukaryotic cells (Jacobs et al., 1985; Lai et al., 1986; Lin et al., 1985).

Chronic renal insufficiency frequently results in hyporegenerative normocytary and normochromic anaemia which is based on absolute or relative erythropoietin deficiency (Besarab et al., 1987; Eschbach and Adamson, 1985; McGonigle et al., 1984; Segal et al., 1988). Without erythropoietin treatment the majority of the haemodialysis patients require transfusions. The availability of recombinant erythropoietin makes it possible to correct renal anaemia with the physiological active substance. The effectiveness of this substitution therapy has been confirmed worldwide in numerous clinical trials; it is therefore expected that recombinant erythropoietin will become the agent of choice in the treatment of anaemia in patients suffering from renal insufficiency. Another application is in correcting the extended bleeding time of uraemics (Moia et al., 1987). Other possible indications for the use of erythropoietin are forms of anaemia which are not renally caused but also accompanied by a reduced concentration of erythropoietin in the plasma, e.g. in chronic infections and inflammations or tumour anaemia. Other possible indications are anaemia in premature babies and use in autologous blood transfusions in surgical patients.

The clarification of the role of the concentration of erythropoietin in pathological conditions and the broad range of potential applications of recombinant erythropoietin as a therapeutic agent for treating anaemia the underlying cause of which is insufficient endogenous EPO formation results in a greater need for suitable methods, on the one hand, for determining the EPO concentration in the serum or plasma, and on the other hand for determining the biological activity within the scope of quality control of erythropoietin produced by recombinant methods.

The assays used to determine the EPO concentration are divided into bioassays and immunoassays.

At present, direct quantitative determination of erythropoietin is routinely carried out in the majority of cases by immunoassay test methods (DE-A1-30 24 270), especially radioimmunoassay methods (Cotes, 1982; Egrie et al., 1987; Eckardt et al., 1988). These methods are based on the principle of determining the displacement of radioactively labelled EPO from the binding to polyclonal (U.S. Pat. No. 4,254,294) or monoclonal antibodies (against highly purified native EPO or recombinant EPO; cf. for example EP-A2-116 446, U.S. Pat. No. 4,558,005) by means of the EPO contained in the sample. It has also been proposed to use ELISAs (Enzyme-Linked Immunosorbent Assays) or Sandwich ELISAs using monoclonal antibodies (WO-84/03152, Wognum et al., 1989; Goto et al., 1989).

These methods are highly sensitive and are used for clinical routine measurements. Since the measurement of immunoreactivity is based on structural and not biological features of the protein, these assays are unable to distinguish between biologically active and inactive erythropoietin and are thus not suitable for measuring biological activity.

The bioassays used hitherto have, as their principle of measurement, the specific biological activity of erythropoietin as the proliferation and differentiation factor for certain erythroid precursor cells.

At present there are in vivo and in vitro assays available for determining the biological activity of erythropoietin.

One of the commonest bioassays is the so-called PCM assay (polycythaemic mouse assay; Cotes et al., 1961; Erslev et al., 1983). The principle of this assay consists in first giving polycythaemic mice the sample containing EPO, according to a strict procedure, then after a certain interval injecting radioactively labelled iron and after another defined interval calculating the rate of incorporation of the iron, based on the total organism, from the radioactivity measured in the erythrocytes (this is a measurement of the rate of haemoglobin synthesis and hence of erythropoiesis). The PCM assay is reliable but not very sensitive (detection threshold about 50 mU/ml), and is also tiresome and complicated and requires a relatively large number of animals and large amounts of $^{59}$Fe, which makes it unsuitable for routine measurements.

As the basis for a method suitable for measuring erythropoietin in vivo, it was also proposed to measure the dosage-dependent effect of erythropoietin on the reticulocyte population of rats; such an assay is admittedly regarded as less sensitive than the conventional in vivo bioassays, but it can be carried out more quickly thanks to the automatic reticulocyte analysis system (Eder et al., 1989).

The in vitro bioassays, which are generally simpler and more convenient to carry out, measure the activity of EPO in short term tissue cultures of haemopoietic tissue (e.g. from the spleen or bone marrow). One of the measuring principles used relies on monitoring the stimulation of haemoglobin synthesis by the incorporation of radioactively labelled iron (Krystal et al., 1981). This method is relatively insensitive and non-specific; the measurement of the iron concentration is impaired by different concentrations of endogenous iron and transferrin. An alternative measuring principle makes use of the promotion of proliferation brought about by erythropoietin. This can be determined by measuring the rate of incorporation of [3H]-thymidine (Krystal, 1983) or by microscopic counting of certain stages in the division of erythroid precursor cells, e.g. the erythroid colony formation (Haga and Falkanger, 1979). Although the latter method is regarded as more reliable than measuring the incorporation of iron, it is also time consuming and expensive and therefore unsuitable for routine assays.

Improvements to the bioassays carried out in vitro have been proposed, consisting in determining the DNA synthesis of erythroid precursor cells in the presence of erythropoietin by measuring the incorporation of radioactively labelled thymidine, in which the substrates proposed for erythroid precursor cells with high sensitivity to erythropoietin consisted of a specific bone marrow preparation from rabbits (EP-A2-0183 404) or a spleen cell preparation from mice treated with phenylhydrazine (Paul et al., 1987), both available in deep-frozen form. Once these preparations are available the assays are relatively simple to carry out and they also have the advantage of high sensitivity; however, these preparations, which have to be made up from scratch each time, are very expensive to produce.

Another serious disadvantage of these in vitro bioassays which have hitherto been used is their non-specific reaction to hormones with a general growth-inducing effect.

The authors of a comparative analysis of the major biological assays for determining biologically active erythropoietin have come to the conclusion that none of the bioassays available is satisfactory in terms of the need for sensitivity with the minimum possible complexity of method (Krumwieh et al., 1988).

One possible way of determining the biological activity of erythropoietin is to measure the erythropoietin-triggered induction of the differentiation in specific erythroleukaemia cell lines. The Abstract of the published Japanese Patent Application J-59133462 describes a cell line which differentiates to the erythrocyte system in the presence of erythropoietin as a function of the concentration. The proportion of differentiated cells can be determined by the uptake of $^{59}$Fe or by counting the benzidine-positive cells. Since cell lines of this kind replicate autonomously independently of EPO and can only partially be induced to differentiate by EPO, this type of assay requires either laborious counting of differentiated cells/colonies in a semisolid medium or the relatively complex and dangerous measurement of haemoglobin with $^{59}$Fe, which requires protective measures against radiation.

Shiozaki et al., 1990 state that the erythroblast cell line ELM-I-1, obtained from mice in which leukaemia had been induced by X-ray irradiation, is EPO dependent for differentiation and growth. The cell line demonstrates a strong stimulation in the number of haemoglobin-positive cells in the presence of EPO. Methods of analysis based on this parameter are, as already mentioned, complicated and not really suitable for routine assays. The growth dependency observed (1.5-fold stimulation after 1½ days) is based on the cell divisions which the cells will normally go through during their terminal differentiation and therefore does not constitute true growth dependency on EPO. Apart from this, 1.5-fold stimulation of growth is not enough to be used as the basis for quantitative measurement of EPO. Furthermore, the cells show a dependency on Il-3 which is greater than that on EPO, making them unsuitable for use in measuring EPO in body fluids.

There was therefore a need for a bioassay which would be sensitive whilst being easy to carry out.

Such a bioassay has now perfected thanks to the ability of the cell lines according to the invention.

The present invention thus relates, according to another aspect, to a process for determining biologically active erythropoietin using the mouse-erythroblast cell lines according to the invention.

The two cell lines according to the invention designated E 4 and E 31 are suitable for measuring the biological activity of erythropoietin because of their strong dependency on EPO for their survival and replication, which can be demonstrated in two types of assays.

As a result of the demonstrably strong dependency of cell line E 31 on erythropoietin for its proliferation, this cell line is particularly suitable for use in detecting the biological activity of erythropoietin.

Cell line E31 was deposited on Mar. 22, 1990 at the European Collection of Animal Cell Cultures (ECACC), PHLS Centre for Applied Microbiology & Research, Porton Down, Salisbury, Wiltshire, SP40JG, United Kingdom, under Accession No. ECACC No. 90032211 in accordance with the Budapest Treaty.

Although the assay according to the invention should also be suitable for determining the EPO concentration in body fluids, it is essential that the cells used should not respond or should respond only slightly to other haematopoietic growth factors. Investigations have therefore been made to find out whether the growth of E 31 cells can be stimulated by various known haematopoietic growth factors. Experiments carried out with the factors IL-6, M-CSF, G-CSF and GM-CSF produced negative results. Checks were also made to discover whether other growth factors found to have a slight effect on the E 31 cells (IL-3 and LIF) have a synergistic effect with EPO. On the basis of numerous experiments the possibility of any of these factors having a reinforcing effect on EPO was ruled out.

The fact that the cell lines according to the invention express the N-TK-v-src retrovirus (developed from the Moloney mouse leukaemia virus (MoMulV)) and produce small amounts of infectious retrovirus does not affect their suitability for use in bioassays, as the viruses expressed cannot infect human cells, nor are they pathogenic to humans.

As the basis for bioassays using the cell lines according to the invention, preferably the cell line E 31, it is appropriate to use methods in which a cell function can be measured as a measurement of the proliferation of cells using suitable parameters.

Methods suitable for the purposes of the present invention include, for example, those methods in which the DNA synthesis is monitored as a cell function by means of the incorporation of DNA components.

A bioassay using the cell line E 31 may, for example, be carried out by measuring the incorporation of [$^3$H]-thymidine into the DNA, which is a measurement of DNA synthesis and hence of cell proliferation. For this purpose, cells of the E 31 cell line are incubated, in the presence of the sample which is to be investigated for its erythropoietin content, in the presence of tritium-labelled thymidine, the quantity of radioactivity incorporated is measured and from this the concentration of erythropoietin is calculated. Since this assay can be carried out, for example, in 96-well microtitre plates and radioactivity can be determined using cell harvesting equipment and radionuclide counters of various kinds such as betacounters, an assay based on this measuring principle can easily be automated (there are automatic devices available for each step of the process, suitable for handling thousands of samples). Thus, this assay can be used for the routine measurement of the biological activity of erythropoietin, e.g. in the quality control of recombinant EPO. This assay is therefore suitable for clinical investigations in which, as well as or instead of immunological measurement of the erythropoietin content in body fluids, it is necessary to determine the biological activity of this growth factor.

In an alternative form of this test principle the synthesis of DNA can also be monitored as a parameter of cell proliferation as a function of the concentration of EPO, by means of incorporated bromodesoxyuridine (BrdUrd) instead of radioactive thymidine. In principle, the procedure is that cells of the cell line according to the invention are incubated with BrdUrd in the presence of the sample whose EPO content is to be investigated and the quantity of BrdUrd incorporated is measured by the bonding of fluorescent-labelled anti-BrdUrd antibodies. The measurement of the fluorescence which corresponds to the incorporated BrdUrd and is thus a measurement of DNA replication can be monitored as the total fluorescence of a certain number of cells in a fluorescence-ELISA photometer or on a single cell basis (thus making it possible to determine the percentage of dividing cells) in a FACS analyser (Gratzner, 1982; Dolbeare et al, 1983).

Another principle of measurement in which the cell function monitored is the activity of certain enzymes native to the cell depending on cell proliferation and which can be used for the bioassay according to the invention is based on the measurement of dyes which are formed by the reaction of suitable substrates by means of cell enzymes. One method developed on this principle is the tetrazolium salt method (MTT method) in which the concentration of the dye formazan formed by reacting a tetrazolium salt by means of dehydrogenase is measured spectrophotometrically (Hansen et al., 1989). When this principle is applied, using the cell line E 31 according to the invention, the cells are incubated with a stock solution of the substrate in the presence of the sample to be analysed and the concentration of the dye formed is measured photometrically. The results obtained, which are, inter alia, a function of the number of cells, can be used directly to calculate the erythropoietin concentration. This type of assay is highly suitable for automation because automatic microtitre metering and pipetting equipment can be used to set up the tests and the results can be evaluated by means of automatic ELISA photometers. The fine adjustment and automation of an assay based on this principle for use within the scope of the present invention can be carried out by the average person skilled in the art by routine experiments.

In developing a bioassay according to the invention using the [$^3$H]-thymidine method, account was taken of the fact that the most important variables for fine adjustment of such an assay in terms of its sensitivity and the incorporation of a low background are the number of test cells and the concentration of serum in the test medium, whereas other parameters (e.g. the nature of the test medium, any additions of medium which may be required) are defined by the growth requirements of the test cells in mass culture or fixed beforehand by the test principle (e.g. the incorporation of $^3$H-thymidine in microtitre plates) (Beug et al., 1982a; Leutz et al., 1984, 1988; Kowenz et al., 1986). The assay was therefore perfected in particular by varying these two parameters. It was found that slightly different conditions are required for greatest possible sensitivity with a maximum measuring range (e.g. the incorporation of thymidine at saturation doses of EPO compared with non-specific corporation).

The invention is illustrated by means of the following Examples.

EXAMPLE 1

Preparation of erythropoietin-dependent mouse erythroblast cell lines $5 \times 10^6$ nucleus-containing spleen cells were injected intravenously into lethally irradiated CBA-J mice (Keller and Wagner, 1989). Three weeks later the secondary recipient animals were killed and cells from the spleen and bone marrow were purified in semi-solid medium (Keller and Wagner, 1989) in the presence of interleukin-3 (10% conditioned medium of WEHI-3B(D$^-$) cells, purified with DEAE-sepharose; (Keller and Wagner, 1989) and human recombinant erythropoietin (EPO; 1 U/ml). After 10 days large colonies of undifferentiated blast-like cells developed in these cultures, in addition to normally differentiated colonies of erythroid and myeloid origin. More than 15 of these colonies, which could not be found in equivalent bone marrow cultures of control animals, were isolated and expanded in Iscove's modified DMEM supplemented by 10% FBS, 10 mg/ml detoxified BSA and 100 μg of iron-saturated human transferrin, hereinafter referred to as erythroblast medium, which contained 10 U/ml EPO and IL-3 in optimum concentration (cf. above). After an initial period of slow growth, more than 8 of the cultures obtained were grown into mass cultures and finally established as cell lines. Since they originate from single methocel colonies they can be regarded as clonal.

EXAMPLE 2

Determining the erythropoietin dependency of cell lines from secondary N-TK-v-src recipients Within the scope of this Example it was found that two of the cell lines obtained in Example 1 exhibit a strong dependency on erythropoietin for their survival and replication. This was demonstrated in two ways:

a) The cells obtained were washed twice in erythroblast medium without growth factors and seeded out at the rate of $1 \times 10^6$ cells/ml in erythroblast medium with or without 10 U/ml EPO contained therein. In a parallel test the cells were cultivated with the addition of IL-3 (10% of a medium conditioned by WEHI3B-(D$^-$), see above) instead of EPO. After various culture times the cells were counted in a Coulter counter and then seeded out again at a density of $1 \times 10^6$ cell/ml. Cumulative cell numbers were calculated from the dilution factor which was obtained by diluting the cells to $1 \times 10^6$ every 1 to 2 days. The results obtained were recorded against the culture time.

Figure 1A:
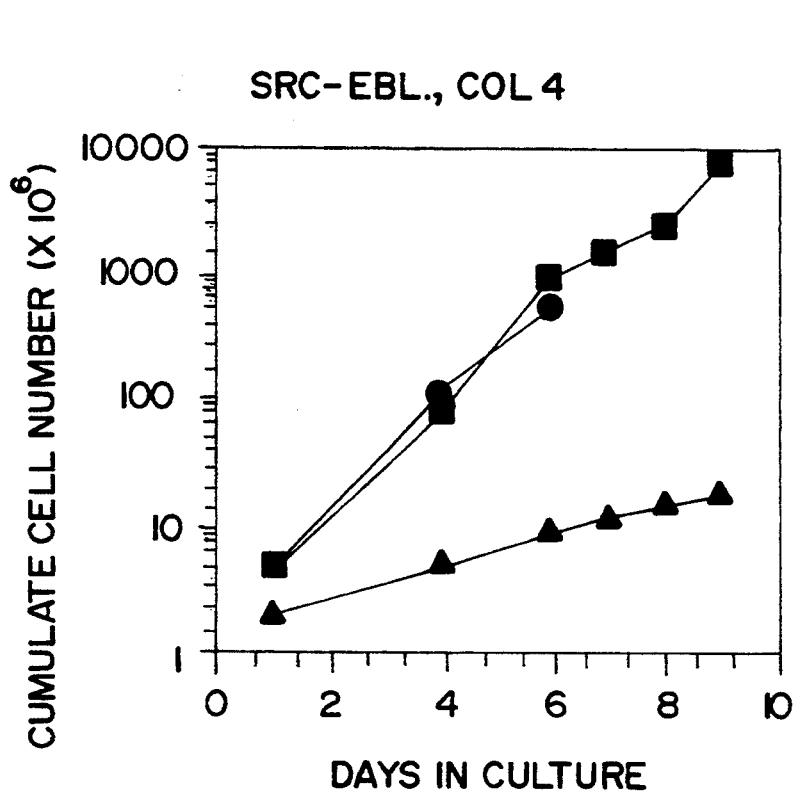
FIG. 1A, B: Stimulation of the proliferation of N-TK-src induced haematopoietic cells by EPO and IL-3.
Figure 1A:
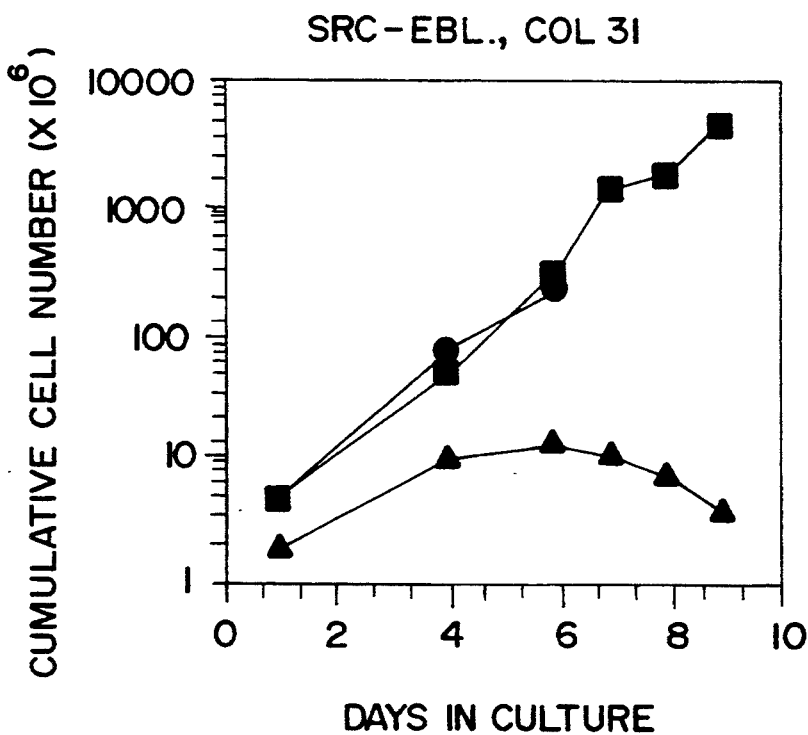

FIG. 1A shows that cells from both lines grew exponentially in the presence of both EPO (squares) and IL-3 (circles). By contrast, slow growth (cell line E 4, designated src-ebl., col 4 in the FIG.) or total stoppage of growth followed by disintegration of the cells (cell line E 31, designated src-ebl., col 31 in the Figure) was observed in the absence of growth factors (triangles).

Figure 1B:
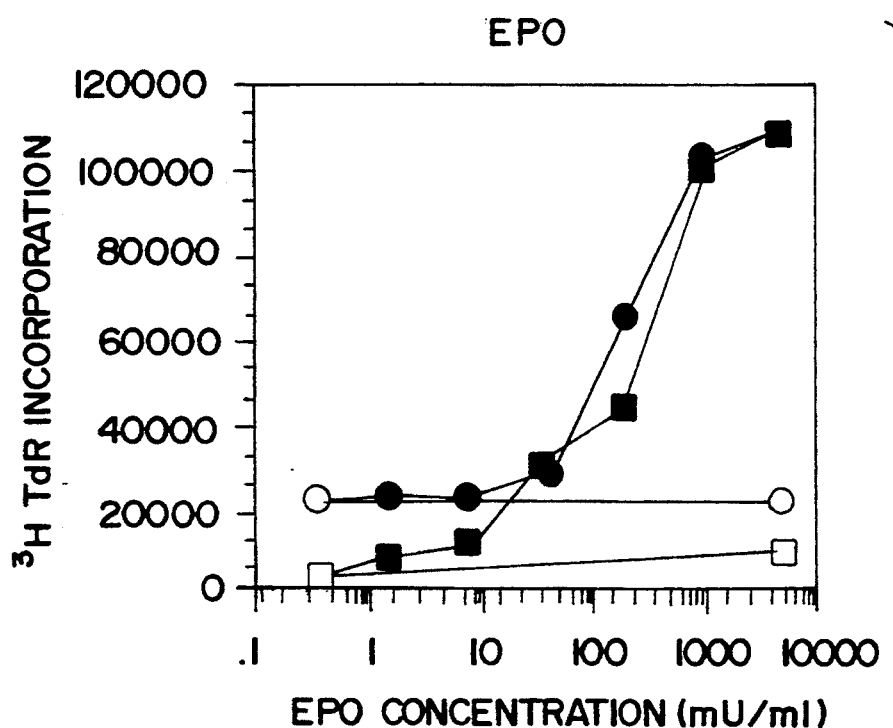
Figure 1B:
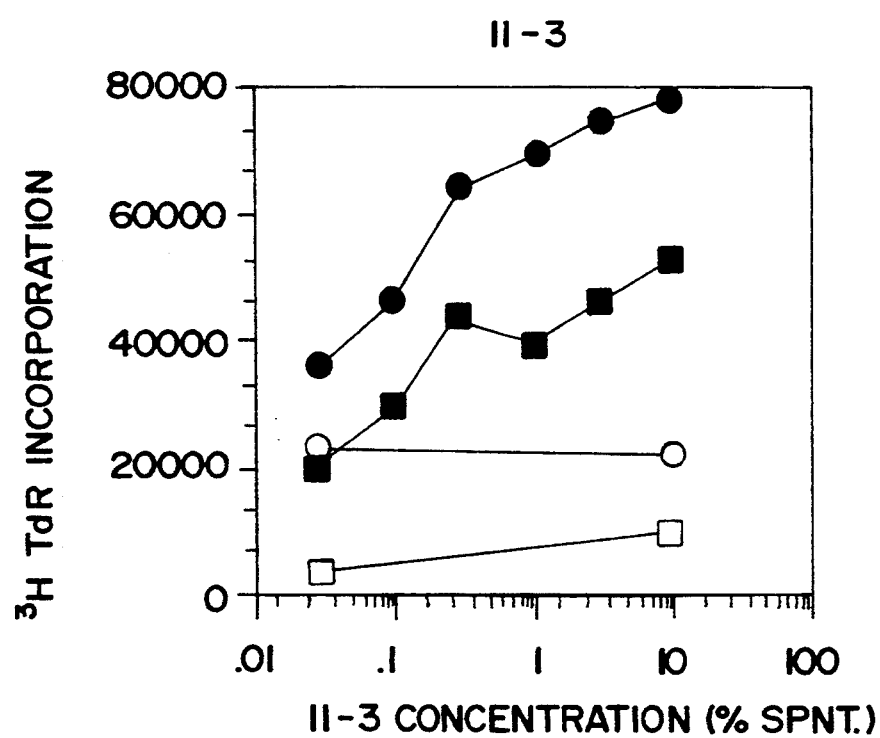

In the second assay type the incorporation of [$^3$H]-thymidine into the DNA was measured, using 96-well microtitre plates and an automatic cell harvesting device (cell harvester, Skatron, Leutz et al., 1984). In these tests, the results of which are shown in FIG. 1B, serial dilutions of EPO (left-hand panel, closed symbols) or of IL-3 (right-hand panel, closed symbols) were prepared starting with 5 U/ml EPO or 10% conditioned medium of WEHI 3B-(D$^-$) cells (containing IL-3) in erythroblast medium (final volume 100 μl). Cells of the cell line E 4 (circles) and E 31 (squares) were added to these dilutions in a final density of $3 \times 10^5$ cells per ml (corresponding to 30,000 cells per well) (volume added 10 ml). As a control, erythroblast medium was subjected to the same procedure (open symbols). After 48 hours at 37° C. the cells were labelled for 2 hours with 0.8 μCi/ml of [$^3$H]-thymidine (specific activity: 19 Ci/mMol; Amersham), filtered on fibre-glass filters in a Skatron cell harvester (Leutz et al., 1984) and the radioactivity incorporated was measured in a β-counter. FIG. 1B shows that EPO intensifies the incorporation of E 4 cells by a factor of 6 to 7 and into E 31 cells by a factor of 30, whereas IL-3 results in only a 3 to 10-fold increase in these cell lines. These results show the strong dependency of both cell lines on erythropoietin.

Analogously, as described for E 4 and E 31, the cell lines E 19, E 25 and E 48, which also originated from single methocel colonies, were investigated for their dependency on these two growth factors (EPO, Il-3). Cell line E 19 proliferated at high cell densities independently of EPO, whereas the other two cell lines resembled the cell line E 4 in their EPO dependency.

EXAMPLE 3

Figure 2A:
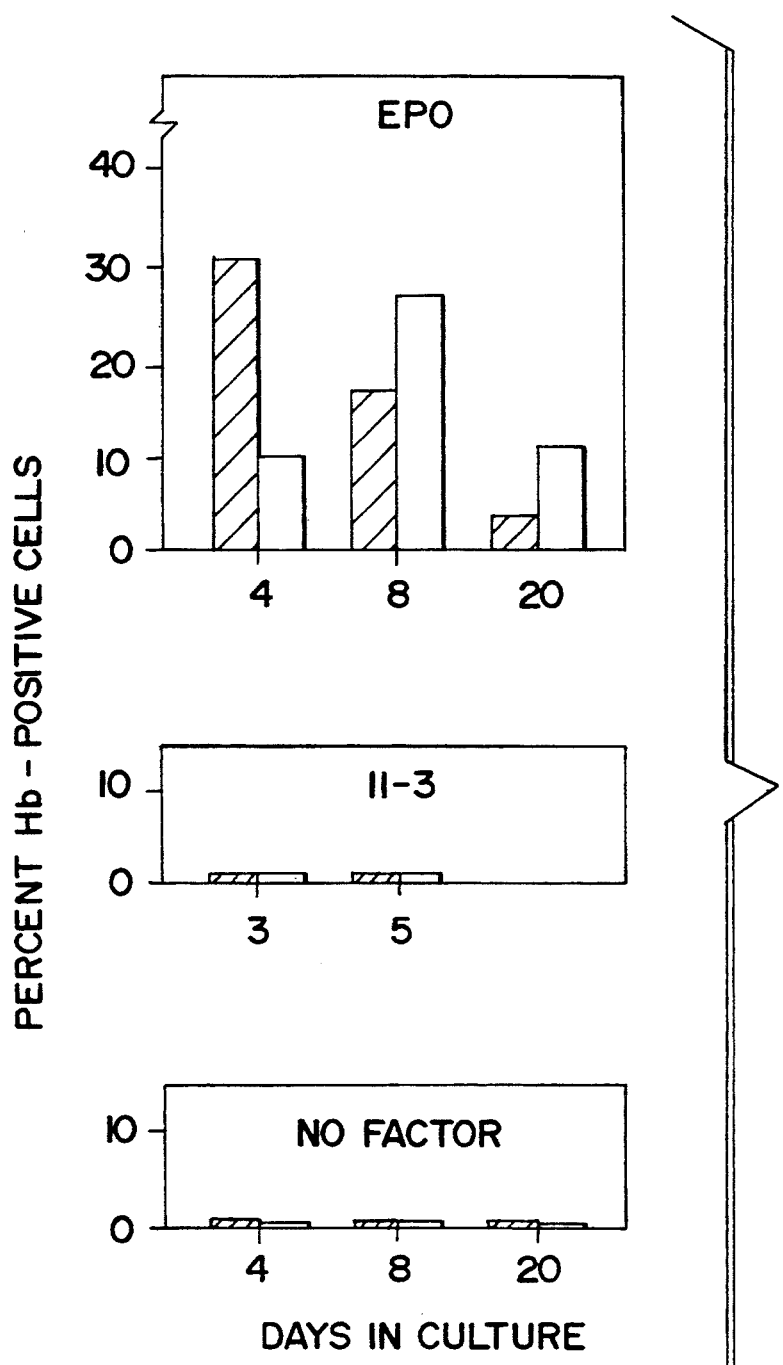
FIG. 2A, B, C: Expression of haemoglobin in the cell lines E4 and E31
Figure 2B:
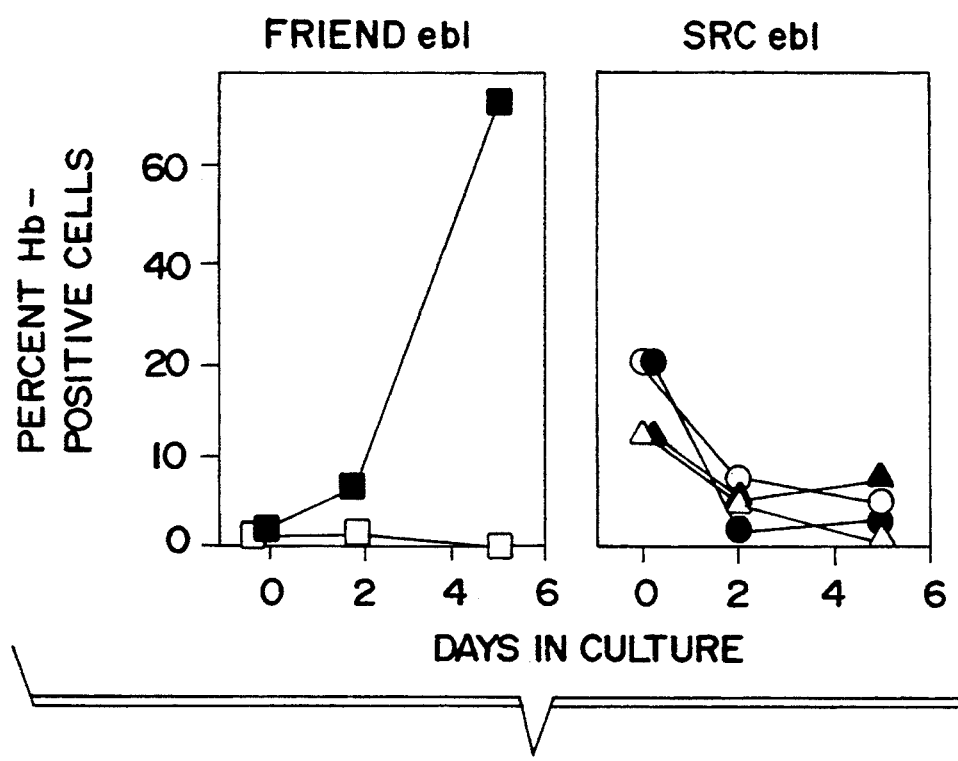

Characterisation of cell lines E 4 and E 31 with regard to the state of differentiation of the cells a) Investigation for haemoglobin To detect haemoglobin the highly sensitive method of acidic benzidine staining was used, which makes it possible to measure 0.1 to 1 μg of haemoglobin per mg of protein on a single cell basis (Orkin et al., 1975, Graf et al., 1978). The results of these tests are shown in FIG. 2A, indicating the percentage proportions of blue stained cells (=haemoglobin-positive cells): E 4 cells (shaded bars) and E 31 cells (dotted bars) were grown at a cell concentration of $1 \times 10^6$/ml erythroblast medium with 5 U/ml of recombinant erythropoietin (at the top), 10% IL-3 containing WEHI 3B-(D$^-$) medium (centre) or with no added growth factors (bottom) and the cells were subjected to acidic benzidine staining using the method described by Graf et al., 1978. FIG. 2A shows that over a period of 20 days in culture both cell lines contained 10 to 30% haemoglobin-positive cells when grown in the presence of erythropoietin. This result rules out the possibility of the haemoglobin-producing cells belonging to a non-growing subpopulation of cells, since such a subpopulation would have been diluted out during culture. Interestingly, the cells which grew in the absence of IL-3 or which survived in the absence of the factors under investigation, produced no haemoglobin (FIG.2A). This results leads one to suppose that these cells require erythropoietin not only for their replication but also for the synthesis of haemoglobin. This assumption is confirmed by the observation that cell populations grown for 7 days in medium which contained IL-3 and having less than 0.1% benzidine-positive cells, had 17% benzidine-positive cells after induction by transferring the cells into medium which contained EPO.

b) In order to attempt to induce haemoglobin production by means of chemicals, Friend erythroleukaemia cells (squares), E 4 cells (circles) and E 31 cells (triangles) were each grown at a concentration of $1 \times 10^6$/ml in erythroblast medium with the addition of (closed symbols) or in the absence of (open symbols) 2% dimethylsulphoxide (DMSO). FIG. 2B clearly shows that the E 4 cells and E 31 cells did not respond to DMSO at all, whereas cultures of Friend erythroleukaemia cells used as control had 80% benzidine positive cells after 5 days of DMSO treatment.

Figure 2C:
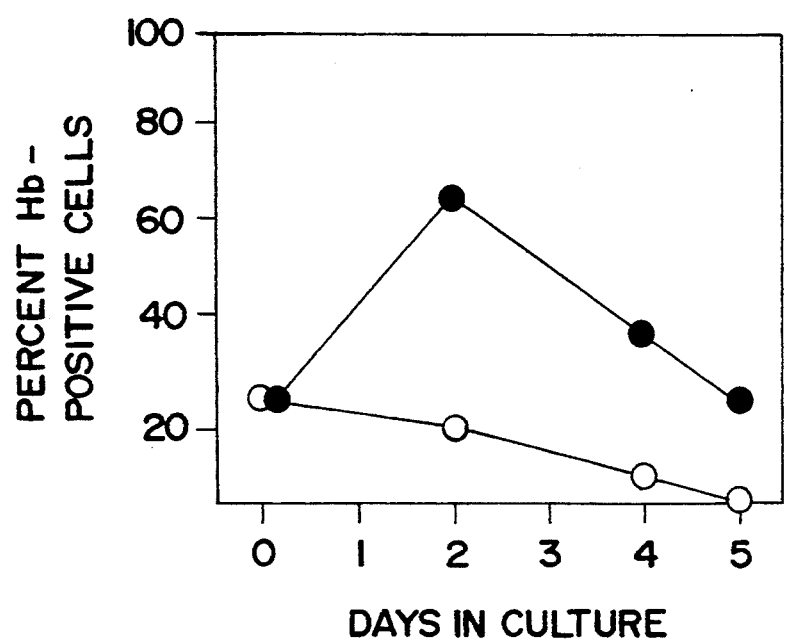
Figure 3A:
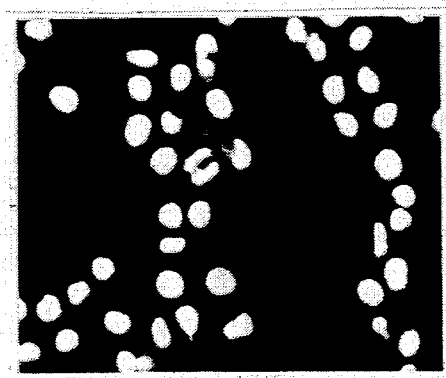
FIG. 3A, B,C, D: Expression of a nucleoprotein which cross-reacts with hen's histone H5
Figure 3B:
Figure 3C:
Figure 3D:
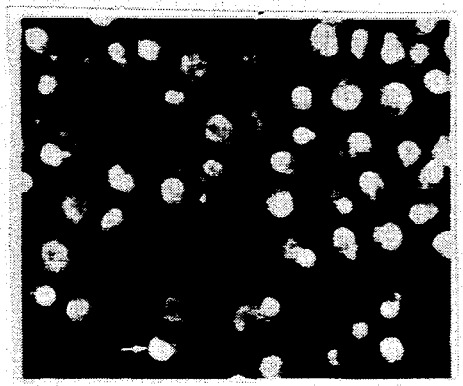

However, after 2 days of butyric acid treatment, the E 31 cells had more than 65% benzidine-positive cells. (FIG. 2C: closed circles: addition of 0.4 mM butyric acid; open circles: no butyric acid added; measurement of the percentage of haemoglobin-positive cells at the times indicated).

c) Investigation into the presence of a protein which cross-reacts with anti-histone H 5 antibodies Antibodies against the erythroid-specific chicken histone H 5 were used as the second independent marker for the erythroid lineage (Beug et al., 1979). Preliminary tests had shown that polyclonal antisera against this histone cross-react with a nuclear antigen in mouse erythroleukaemia cells. In order to demonstrate that this cross-reacting nuclear protein (probably a histone of the "replacement variant" types such as H1-0) is expressed only in erythroid cells, the following procedure was used (cf. FIG. 3): chicken erythroblasts (HD 3-cells, Beug et al., 1982b) (A), a 1:1 mixture of Friend erythroleukaemia cells with the same number of myeloid leukaemia cells (Wehi 3B-(D$^-$)) (B), E 4 erythroblasts (C) and E 31 erythroblasts (D) were cytocentrifuged on slides and labelled with anti-H 5 rabbit antiserum (rabbit 50, 1st bleeding, other bleedings from the same rabbit or other sera were not as suitable) with indirect immunofluorescence, precisely as described by Beug et al., 1979, with the sole difference that the washing buffer contained 0.1% bovine serum albumin plus 0.1% gelatine. FIG.3B shows that the small cells (the Friend erythroleukaemia cells) exhibited nuclear fluorescence, whilst the other, normally larger cells (WEHI 3 B-(D$^-$) cells) were negative (short arrows in B, C and D: cells with significant nuclear fluorescence; long thin arrows in B: WEHI 3B-(D$^-$). As expected, the intensity of fluorescence of the positive nuclei in the small mouse erythroleukaemia cells was much less than in the v-erb B transformed chicken erythroblasts which are shown as the control in FIG. 3A. Similar mixed experiments carried out with a lymphoid leukaemia cell line gave the same result. From this it can be concluded that the protein detected by the anti-H 5 antibodies is erythroid-specific. When cells of the E 4 and E 31 line (marked in the Figure as src-ebl.col 4 and src-ebl.col 31, respectively) were labelled with the same anti-H 5 antibodies, between 80 and 90% of the cells exhibited significant nuclear fluorescence, the negative cells presumably being the cells damaged by cytocentrifugation (FIGS. 3C, 3D). Together with the results shown under a), this finding indicates that the cell lines E 4 and E 31 belong exclusively to the erythroid lineage.

d) Investigation for other markers

In order to rule out the possibility of the E 4 and E 31 erythroblast cell lines containing cells from other lineages, they were stained as living cells, in indirect fluorescence, with a number of monoclonal antibodies which recognise myeloid-specific cell surface antigens (Mac-1, Mac-2), antigens of pluripotent stem cells (Sca-1) or, as a control, an antigen which is present on all haematopoietic cells apart from thymocytes (J11D). These experiments were carried out precisely as described by Kornfeld et al., in 1982 for chicken cells, with the exception that the cells ($1 \times 10^6$ per sample) were saturated with goat serum (10% in test medium) before the incubation with monoclonal antibody in order to block Fc-receptors. The monoclonal antibodies were used at optimum dilutions (from 1:10 to 1:50) determined on corresponding control cells. Observation under a fluorescent microscope and FACS analysis showed that neither of the two cell lines expresses detectable quantities of any of the cell surface antigens which are recognised by the cell-type-specific monoclonal antibodies, i.e. which are specific to non-erythroid cells, but that cells of both lines were strongly stained with the control antibody. This result also confirms the correctness of the assumption that the cell lines E4 and E 31 contain only cells of the erythroid lineage.

EXAMPLE 4

Detection of integrated provirus, virus expression and expression of the src-oncogene By Southern blot analysis in order to detect integrated proviruses, carried out as described by Keller and Wagner, 1989, it was shown that the cells of the E 4 and E 31 lineage contain a single copy of the integrated N-TK-v-src provirus. By measuring the tyrosine kinase activity in immunoprecipitates of cell lysates using an anti-v-src-antibody, carried out as described by Keller and Wagner, 1989, it was demonstrated that the cells express the v-src protein in amounts which are 10 to 100 times greater than the expression rate of the cellular c-src protein. As described for the infection of NIH-3T3 cells (Keller and Wagner, 1989), it was shown by selection on neomycin-resistant colonies that the cells express small amounts ($<10^2$ infectious units per ml of cell supernatant) of infectious retrovirus derived from N-TK-v-src.

EXAMPLE 5

Development of an erythropoietin bioassay using the E 31 cell line

Figure 4A:
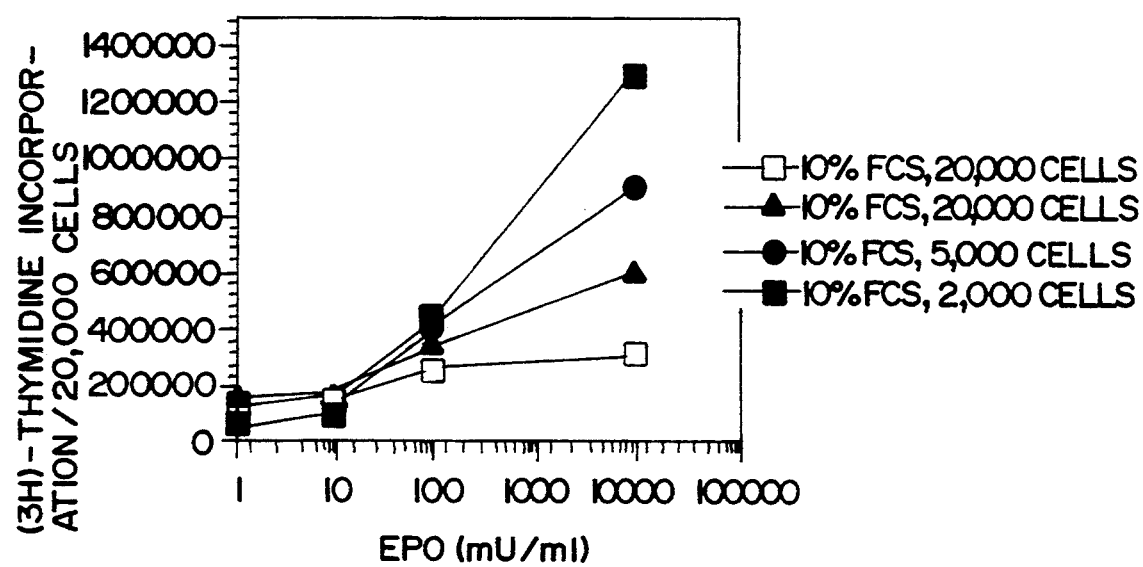
FIG. 4A, B: Optimising the conditions for a bioassay for EPO using the cell line E31

In order to optimise the assay the number of test cells and the serum concentration in the test medium were varied. In order to do this, different numbers of E 31 cells ($2 \times 10^3 - 2 \times 10^4$ cells per well, see FIG. 4) were seeded in erythroblast medium with the specified amount of EPO (1 mU corresponds to no addition of EPO) in the presence of 10% (A) or 2% (B) FCS. The incubation for 72 hours at 37° C., the labelling with [$^3$H]-thymidine and the harvesting of the cells were carried out as described in Example 2. The results (FIG. 4) show that different conditions are required for maximum sensitivity (detectable stimulation of the incorporation of thymidine at the lowest possible EPO concentrations) or for the largest possible measuring range (maximum incorporation of thymidine at saturation doses of EPO as against non-specific incorporation). For example, under a certain set of conditions (high concentration of foetal calves' serum (10%) and low numbers of cells ($2 \times 10^4$ cells/ml) 10 mU EPO will still bring about a stimulation of thymidine incorporation which is 2.5 times the base level, but only a maximum stimulation of 25 times at the saturation concentration of EPO (M0 U/ml (FIG. 4A). By contrast, when low concentrations of foetal calves' serum were used (2%) and higher numbers of cells (0.5 to $1 \times 10^5$ cells per ml) with saturation doses of EPO, an 80 to 240-fold increase in incorporated thymidine was achieved compared with the base value. Whilst this value was substantially higher than the maximum stimulation (25-fold increase) obtained at a high serum concentration, the sensitivity of the assay was much lower under these conditions (it was only possible to measure the EPO concentration accurately in the range between 20 to 50 and 1,000 mU EPO). The optimising of other parameters (carried out in previously experiments) such as the volume of the culture (100 μl), the concentration of the radioactivity (0.8 μCi/ml), the period of incubation before labelling (48 hours for high cell concentrations) 72 hours for low cell concentrations), the labelling time-(2 hours) and the addition of other components (such as insulin) to the test medium (erythroblast medium) produced results corresponding to those for assays using other types of cell (Leutz et al., 1984), and consequently these parameters need not be analysed any further.

EXAMPLE 6

Check as to whether E 31 cells respond to other growth factors

Figure 5:
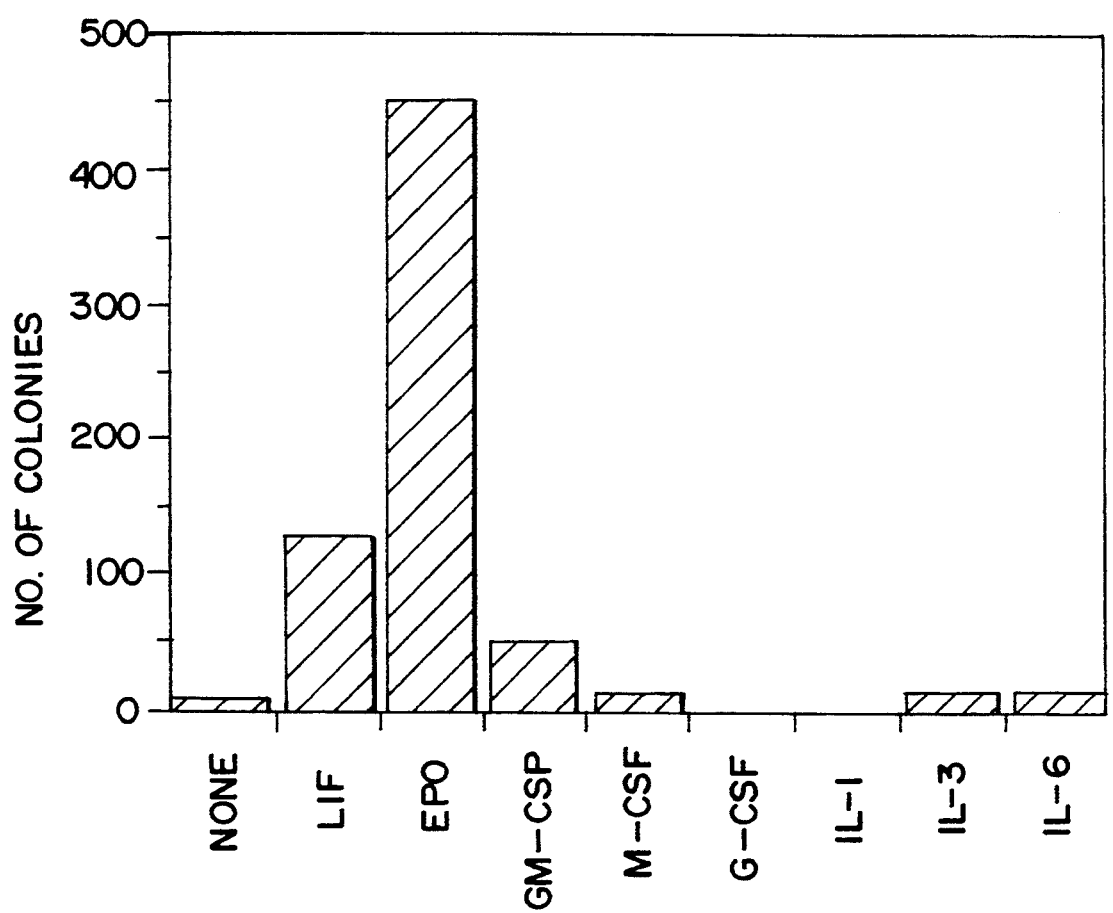
FIG. 5: Check as to whether E31 cells respond to other growth factors

In preliminary tests, it was established that under conditions such as those used in the experiments described in FIGS. 1B and 4A, apart from IL-3 only leukaemia inhibitory factor (LIF) brought about a slight increase in the incorporation of thymidine into E 31 cells, whilst the other factors tested (IL-6, M-CSF, G-CSF and GM-CSF) gave negative results (see FIG. 5). In order to check this more accurately, E 31 cells were seeded in the presence of saturation doses of EPO (10 U/ml) or other growth factors (IL-3: 10% conditioned medium of Wehi-3B-(D⁻) cells; LIF: 1000 U/ml of recombinant human LIF; M-CSF: 20% L-cell conditioned medium (Stanley and Heard, 1977) or 1000 U/ml of recombinant human M-CSF; G-CSF: 10% DIND-1 cell conditioned medium; IL-6: 100 U recombinant IL-6; GM-CSF: 15% condition medium of the human bladder carcinoma cell line 5637) in semisolid medium (Methocel) and a number of colonies consisting of more than 1000 cells was counted 12 days later. This test is even more sensitive than that described in Example 5.

Figure 4B:
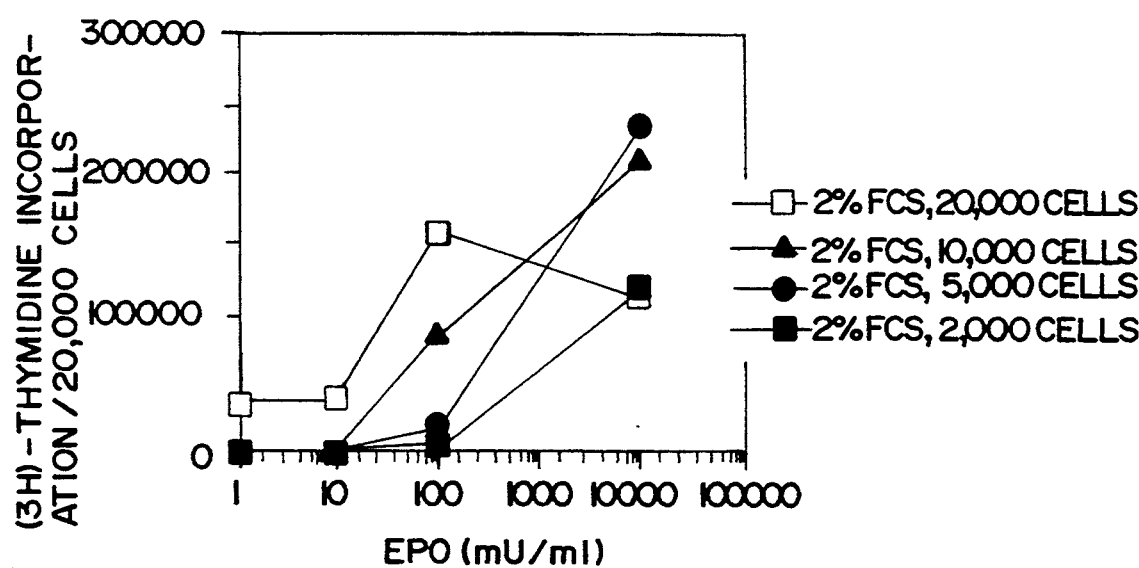

In order to check whether other growth factors which exhibit a slight effect on E 31 cells have a greater activity in the presence of low doses of EPO, i.e. having a synergistic effect with this hormone, different amounts of IL-3 (0.01 to 10% conditioned-Wehi-3B-(D⁻) medium and LIF (0.1 to 100 U/ml recombinant LIF) were mixed with a constant amount of EPO which has very little effect on its own (10 mU; cf. FIGS. 1 and 4) and the effect on the proliferation of E 31 cells was investigated in the [$^3$H]-thymidine assay as described in FIG. 4, but with a constant number of cells ($2 \times 10^4$) and decreasing amounts of FCS (10 to 0.5%). It was established in numerous experiments that neither LIF nor IL-3 when combined with EPO results in any more than an additive stimulation of thymidine incorporation. Thus, the possibility of these factors having an intensifying effect on EPO can be ruled out.

BIBLIOGRAPHY

Besarab, A. et al., 1987, Kidney Int. 32, 526
Beug, H. et al., 1982a, Cell 28, 907–919
Beug, H. et al., 1982b, J. Cell Physiol. Suppl. 1, 195–207
Beug, H. et al., 1985, Modern Trends in Human Leukaemia VI. (Neth, R. et al. Eds.), Springer Verlag, Berlin-Heidelberg, 29, 290–297
Cotes, P. M. et al., 1961, Nature 4793, 1065–1067
Cotes, P. M. et al., 1982, Br. J. Haemat. 50, 427–438
Dolbeare, F. et al., 1983, Proc. Natl. Acad. Sci. U.S.A. 80, 5573–5577
Eckardt, K. U. et al., 1988, Klin, Wschr. 66, 241–245
Eder H., et al., 1989, Blut 59, 184–187
Egrie J. C., et al., 1987, J. Immunol. Methods 99, 235–241
Erslev A. J., et al., 1983, Hematology, 3rd Ed., 1634
Eschbach J. W. et al., 1985, Kidney Int. 28, 1
Goto, M. et al., 1989, Blood, Vol. 74, No.4, 1414–1423
Graf, T. et al., 1978, Nature 275, 496–501
Gratzner, H. G., 1982, Science, Vol 218, 474–475
Haga and Falkanger, 1979, Blood 53, 1172
Hansen, M. B. et al., 1989, J.Immunol.Methods 119, 203–210
Jacobs, K. C. et al., 1985, Nature 313, 806
Keller, G. and Wagner, E. F., 1989, Genes and Dev. 3, 827–837
Kowenz, E. et al., 1986, Modern Trends in Human Leukemia VII (Neth et al., Eds.), Springer-Verlag Berlin, 31, 199–209
Kornfeld, S. et al., 1983, Exptl. Cell Res. 143, 383–394
Krumwieh, D. et al., 1988, Develop. Biol. Standard., Vol 69, 15–22
Krystal, G. et al., 1981, J.Lab. Clin. Med. 97, 144
Krystal, G. et al., 1981, J.Lab. Clin. Med. 97, 144–157
Krystal, G. 1983, Exp. Hematol. 11, 649
Lai, P. H. et al., 1986, J. Biol. Chem. 261, 3116
Leutz, A. et al., 1984, EMBO J. 3, 3191–3197

Leutz, A., et al., 1988, J. Biol. Chem. 263, 3905–3911
Lin, F. K. et al., 1985, proc. Natl. Acad. Sci. U.S.A. 82, 7580
McGonigle, R. J. et al., 1984, Kidney Int. 25, 437
Miyake T. C. et al., 1977, J. Biol. Chem. 252, 5558
Moia, M. P. et al., 1987, Lancet II, 1228
Orkin, S. H. et al., 1975, Proc. Natl. Sci. U.S.A. 72, 98–102
Paul, Ph. et al., 1987, Exp.Hematol. 15, 382–388
Segal, G. M. et al., 1988, Kidney Int. 33, 983
Shiozaki, M. et al., Leuk. Res. 14, 287–291
Stanley, E. R. and Heard P. M., 1977, J. Biol. Chem. 252, 4305–4312
Wognum, A. W. et al., 1989, Blood, Vol. 74, No.2, 622–628

We claim:

1. The erythroblastoid mouse cell line E 31, deposited as ECACC No. 90032211.

* * * * *